United States Patent
Siedel et al.

[11] Patent Number: 6,013,467
[45] Date of Patent: Jan. 11, 2000

[54] BLOOD SUBSTITUTE SUPPRESSION BY PEROXIDES

[75] Inventors: Joachim Siedel, Tutzing; Michael Harold Town, Oberhausen; Christian Birkner, Uffing, all of Germany

[73] Assignee: Boehringer Mannheim GmbH, Mannheim, Germany

[21] Appl. No.: 09/147,531

[22] PCT Filed: Jul. 14, 1997

[86] PCT No.: PCT/EP97/03750

§ 371 Date: Mar. 17, 1999

§ 102(e) Date: Mar. 17, 1999

[87] PCT Pub. No.: WO98/02570

PCT Pub. Date: Jan. 22, 1998

[30] Foreign Application Priority Data

Jul. 15, 1996 [DE] Germany .............. 196 28 484

[51] Int. Cl.[7] .............. C12Q 1/26; C12Q 1/40; C12Q 1/42; C12Q 1/48; C12Q 1/00
[52] U.S. Cl. .............. 435/25; 435/22; 435/21; 435/15; 435/4; 435/975
[58] Field of Search .............. 435/25, 22, 21, 435/15, 4, 975

[56] References Cited

U.S. PATENT DOCUMENTS

| | | | |
|---|---|---|---|
| 4,252,783 | 2/1981 | Kam et al. | 424/8 |
| 4,673,654 | 6/1987 | Talmage | 435/28 |
| 4,695,552 | 9/1987 | Schmitt | 435/28 |
| 4,978,632 | 12/1990 | Mach et al. | 435/7 |

FOREIGN PATENT DOCUMENTS 0 693 552 A2  1/1996  European Pat. Off. .

OTHER PUBLICATIONS

International Publication No. WO 90/02202 published Mar. 8, 1990.
International Publication No. WO 86/07462 published Dec. 18, 1986.

*Primary Examiner*—Louise N. Leary
*Attorney, Agent, or Firm*—Nikaido, Marmelstein, Murray & Oram LLP

[57] ABSTRACT

The invention concerns a method for the elimination or/and reduction of interferences which are caused by the presence of free haemoglobin in the determination of an analyte in a sample by optical measurement, wherein one or several peroxidic compounds are added to the analytical reagent or to a part thereof before the measurement. In addition a reagent kit is disclosed which contains at least one peroxidic compound.

21 Claims, 7 Drawing Sheets

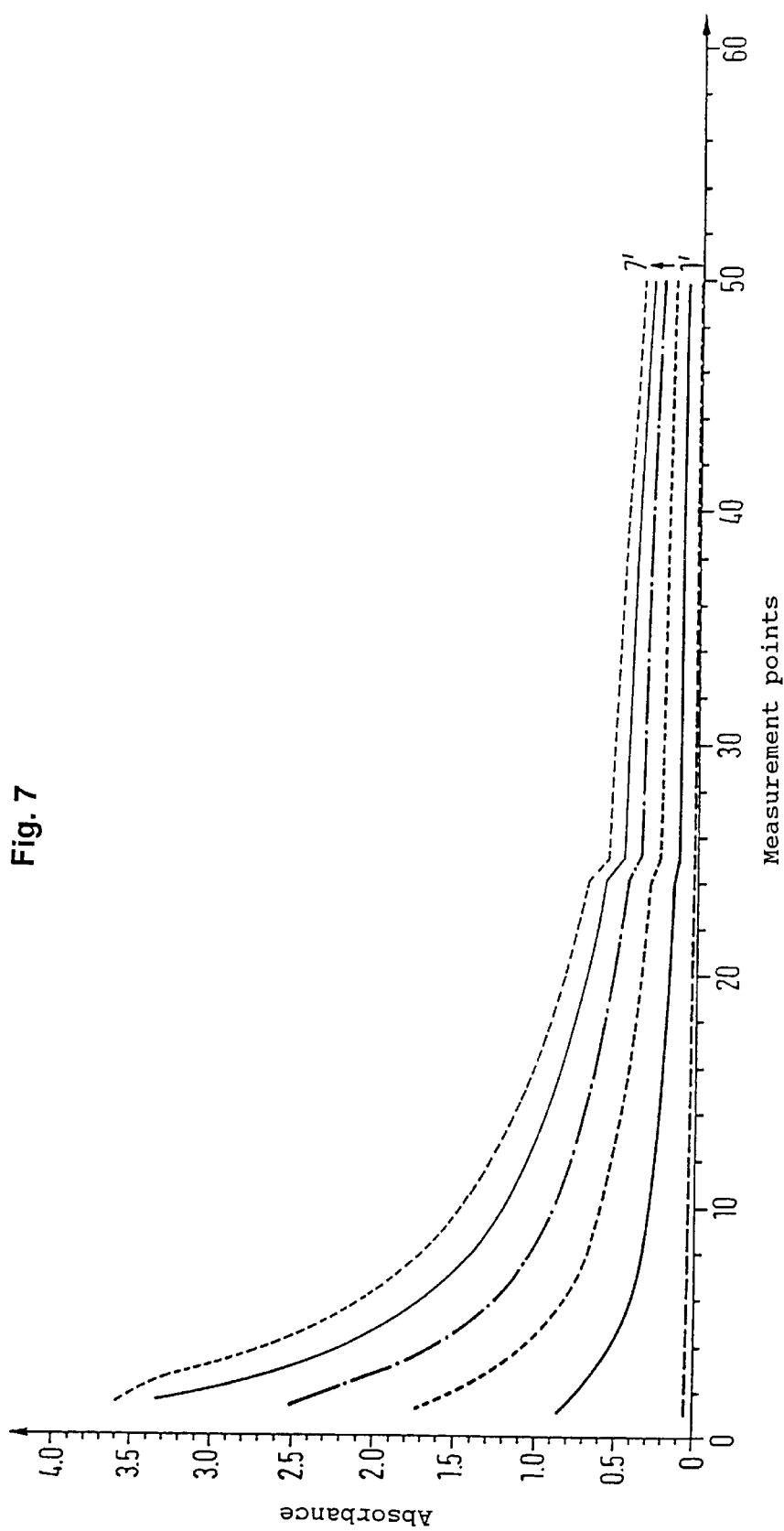

BLOOD SUBSTITUTE SUPPRESSION BY PEROXIDES

The invention concerns a method for the determination of an analyte in a sample containing free haemoglobin by optical measurement with the addition of a bleaching agent to the analytical reagent. This method is particularly suitable for the determination of components of a medical sample such as the parameters α-amylase, alkaline phosphatase and γ-glutamyl transferase in a blood, serum or plasma sample.

A frequent occurrence when determining components of clinical-diagnostic relevance in blood, serum and plasma samples is that these sample materials contain free haemoglobin i.e. they are haemolytic. This haemolysis can either be due to native haemoglobin released from the erythrocytes or the therapeutic administration of blood substitutes based on non-cellular haemoglobin derivatives.

In many cases the analysis of such samples containing haemoglobin is disturbed or made completely impossible, especially when using photometric methods of determination, mainly due to the spectral properties of haemoglobin or haemoglobin derivatives. This is especially the case when the photometric measurement is carried out at a wavelength at which a strong absorption of haemoglobin takes place for example at wavelengths between ca. 400–420 nm and if at the same time a high content of haemoglobin is present in the sample i.e. usually>500 mg/dl.

The availability of blood substitutes based on haemoglobin derivatives poses the problem of eliminating such analytical interference caused by haemolysis to a much greater extent than previously. After their therapeutic administration, haemoglobin levels of up to ca. 2000 mg/dl can occur in the blood serum or blood plasma and the situation is aggravated by the fact that in this case it is not possible to avoid the presence of free haemoglobin in the sample even by suitable precautionary measures when serum or plasma is obtained from the blood sample.

There is therefore a need for a method which enables photometric determinations of diagnostically important analytes to be carried out without interference even in strongly haemolytic serum or plasma samples containing for example blood substitutes up to concentrations of at least 2000 mg/dl.

The object of the invention was achieved by a method for eliminating or/and reducing interferences that are caused by the presence of free haemoglobin in the determination of an analyte in a sample by optical measurement in which one or several peroxidic compounds are added to the reagent used to determine the analyte or to a part thereof.

The addition according to the invention of peroxidic compounds to the analytical reagent or to one or several partial reagents enables on the one hand an elimination of spectral interference by the haemoglobin present in the sample. On the other hand it was also possible to eliminate interference caused by interactions of haemoglobin with other substances present in the sample.

The reagent which is added to the sample can be in a liquid or solid form. In the case of analyte determinations which are carried out in a liquid phase, it is also preferable to add a liquid reagent to the sample. However, in dry tests the reagent can also be present in a solid form e.g. in the form of impregnated fibres or fleeces.

Inorganic as well as organic peroxides come into consideration as the peroxidic substances. Inorganic peroxidic compounds are preferred such as $H_2O_2$, peroxides, perborates, persulfates, peroxodisulfates, percarbonates etc. The peroxidic compounds are particularly preferably selected from the group comprising $H_2O_2$ and perborates such as $NaBO_2 \times H_2O_2 \times 3H_2O$ or $Na_2B_4O_7 \times H_2O_2 \times 9H_2O$.

The final concentration of the peroxidic compounds in the test mixture can be varied over a wide range. It is preferably 1–500 mmol/l and particularly preferably 5–200 mmol/l with reference to the content of $O_2^{2-}$ in the test mixture.

The addition of peroxidic compounds leads to a rapid bleaching of the colour caused by the haemoglobin or haemoglobin derivative after mixing the sample with the analytical reagent without at the same time significantly impairing a subsequent determination in the same reaction mixture of the analyte such as e.g. an enzyme by means of chromogenic substrates. This finding is very surprising since in no way could it have been foreseen that peroxidic compounds do not influence enzymatic activities and/or interfere with the respective indicator reaction even at relatively high concentrations and within the usual temperature range used for photometric serum and plasma analyses i.e. in general from 25 to 37° C., even over a relatively long duration of action i.e. preferably for at least 1 min and particularly preferably for at least 2–10 min.

The method according to the invention is especially suitable for optical measurements which are carried out at at least one measurement wavelength at which native haemoglobin or synthetic haemoglobin derivatives have an absorption. The method is particularly preferably carried out with optical measurements in the measurement wavelength ranges of about 380–450 nm and in particular of 400–420 nm or/and 520–590 nm where haemoglobin has its main and secondary absorptions.

The method according to the invention is suitable for the determination of any samples in which free haemoglobin is present. Examples of such samples are native haemolytic blood, serum or plasma samples or samples which contain a blood substitute based on haemoglobin derivatives. Examples of blood substitutes which are covered in the sense of the present invention by the term "free haemoglobin" are modified or intramolecularly or intermolecularly cross-linked or polymerized derivatives of haemoglobins especially of human haemoglobin or bovine haemoglobin e.g. DCL-haemoglobin (diaspirin cross-linked haemoglobin) as well as recombinant haemoglobin muteins obtained for example from microorganisms (cf. e.g. Blood substitutes, R. M. Winslow, K. D. Vandegriff, M. Intaglietta (editor), Birkhauser, Boston 1995 and EP-A-0700 997). In a particular embodiment of the method according to the invention the analyte to be determined is an enzyme. Preferred enzymes are selected from the group of hydrolases such as e.g. α-amylase, alkaline phosphatase and γ-glutamyl transferase (γ-GT). In addition the method according to the invention is also suitable for the determination of other analytes.

A medical sample e.g. a blood, serum or plasma sample is preferably used as the sample in the method according to the invention and in particular a human serum or plasma sample.

A particular advantage of the method according to the invention is that it can be carried out in an automated analyser e.g. a Boehringer Mannheim/Hitachi 704 or 717 analyser.

In a preferred embodiment, the analyte is determined in the method according to the invention as a multi-step test e.g. as a two-step test in which at least two partial reagents are added successively at different times to the sample. In such a multi-step test procedure, the peroxidic compounds can be preferably added to the partial reagent which is added first to the sample. The actual analyte determination is then preferably carried out at the earliest after addition of the second partial reagent which for example in the case of an enzyme determination can contain a chromogenic colour substrate.

If in a multi-step test procedure the peroxidic compounds are added together with a first partial reagent, the second or at least one of the other partial reagents can then optionally additionally contain an agent which in turn removes the excess peroxidic compounds derived from the first partial reagent in order to avoid possible interference of other analyses that are subsequently carried out in the same reaction vessel due to so-called carry-over effects.

If $H_2O_2$ or/and perborates are used as the peroxides, the agent for removing the peroxidic compounds preferably contains a peroxide-converting enzyme such as catalase or/and peroxidase optionally together with one or several suitable substrates for the peroxide-converting enzyme.

In addition superoxide dismutase can be additionally added to the analytical reagent or a partial reagent thereof to prevent formation of superoxide radicals $O_2-$.

By means of the method according to the invention it is possible to achieve without further measures a recovery of the analyte to be detected even in haemolytic samples of 100±10% and preferably 100±5% if at the time of the first measurement the bleaching of haemoglobin or the haemoglobin derivative by the peroxidic compounds is essentially completed or has come to a standstill. If, in contrast, the bleaching reaction has not yet come to a standstill at the start of the measurement which may be the case with a very high haemoglobin concentration in the sample and/or with a relatively high sample to reagent volume ratio, then preferably an additional blank value correction can be carried out to achieve the desired analytical accuracy. This blank value correction can for example be carried out by subtracting the blank signal obtained in the same measurement period in a parallel test with a like-wise peroxide-containing but chromogen-free reagent, from the measurement signal which is obtained with the reagent containing peroxide and chromogen. The blank value correction is particularly preferably carried out by subtracting a kinetic blank value.

In a two-step test the blank value is preferably determined by adding a first partial reagent (R1) containing peroxide, preferably a reagent with the same peroxide concentration as in the test mixture, and subsequently a chromogen-free second partial reagent (R2) to the sample and determining the blank value from this test mixture which is then to be subtracted from the measured signal.

A further subject matter of the invention is a reagent kit for the determination of an analyte in a sample by optical measurement which, in addition to the components required to determine the analyte, contains at least one peroxidic compound to eliminate or/and reduce interferences caused by free haemoglobin. The reagent kit is preferably composed of at least two partial reagents that are spatially separated from one another. A partial reagent preferably contains the peroxidic compound separate from all other components. In this partial reagent the peroxidic compound can be present in a solid or liquid form e.g. as a powder or tablet or also as a stabilized solution. The partial reagent containing the peroxidic compound is preferably mixed with a further partial reagent before carrying out the test.

A reagent kit according to the invention for the determination of enzymes preferably contains a first partial reagent containing the peroxidic compound, a further partial reagent that can be mixed with the peroxidic compound and a separate reagent which contains a chromogenic colour substrate.

A reagent kit according to the invention for the determination of α-amylase preferably comprises a first partial reagent which contains the peroxidic compound, a further partial reagent which is compatible with the peroxidic compound which optionally contains an α-amylase auxiliary enzyme such as α-glucosidase or/and an antibody, as well as a further partial reagent which contains a chromogenic α-amylase substrate such as an oligomeric glucoside.

A reagent kit according to the invention for the determination of alkaline phosphatase preferably comprises a first partial reagent containing a peroxidic compound. A further partial reagent which is compatible with the first partial reagent preferably contains a suitable alkaline buffer, and a further partial reagent contains a chromogenic substrate for alkaline phosphatase e.g. a phosphate ester such as 4-nitrophenyl phosphate.

A reagent kit according to the invention for the determination of γ-glutamyl transferase preferably comprises a first partial reagent containing a peroxidic compound, a second partial reagent which contains a suitable buffer and a further partial reagent which contains a chromogenic substrate for γ-GT such as L-γ-glutamyl-3-carboxy-4-nitroanilide.

It is intended to further elucidate the present invention by the attached figures as well as by the following examples.

FIG. 6 shows the time course of the measured signal in a determination of γ-GT in samples containing different amounts of a HB derivative with the addition of a peroxidic compound (1-7) and FIG. 7 shows the time course of the signal for a blank correction (1'-7') carried out in parallel to the experiments in FIG. 6.

EXAMPLES

Example 1

Determination of alkaline phosphatase (AP) in serum containing a haemoglobin derivative.

1.1. Sample Material 0.40 ml aliquots of a human serum pool are supplemented with 0.0–0.10 ml haemoglobin derivative (di-aspirin cross-linked haemoglobin, 'DClHb', 10 g/dl; Baxter Co.) in steps of 0.01 ml and in each case filled up to 0.50 ml with 0.9% NaCl solution to equalize the volume (DClHb concentration 200–2000 mg/dl).

A mixture of 0.40 ml of the same serum pool with 0.10 ml 0.9% aqueous NaCl solution is also run as a control.

1.2. Reagents:

1.2.1. Alkaline phosphatase basic reagent (corresponding to the recommendations of the German Society for Clinical Chemistry)

AP DGKCh (Sys 2 pack, Boehringer Mannheim GmbH, order No. 1 662 902), composition:

| | |
|---|---|
| R1: D(−)-N-methylglucamine HCl (pH 10.1) | 610 mmol/l |
| Mg acetate | 0.61 mmol/l |
| NaCl | 85.4 mmol/l |
| R2: 4-nitrophenylphosphate | 122 mmol/l |

1.2.2. Alkaline phosphatase reagent with peroxide additive:

Like 1.2.1. except that $H_2O_2$ is additionally added to R1 at a concentration of 147 mmol/l (0.5 ml 30% perhydrol per 30 ml R1) ($H_2O_2$ final concentration in the test=120 mmol/l.

1.3. Procedure for the determination

Alkaline phosphatase was determined on a Boehringer Mannheim/Hitachi 717 analyser at 37° C. with the instrument settings according to the working instructions of the package insert (5 μl sample, 250 μl R1, 50 μl R2; wavelengths 700/405 nm; measurement interval 30th–38th measurement point).

1.4. Results

Figure 1:
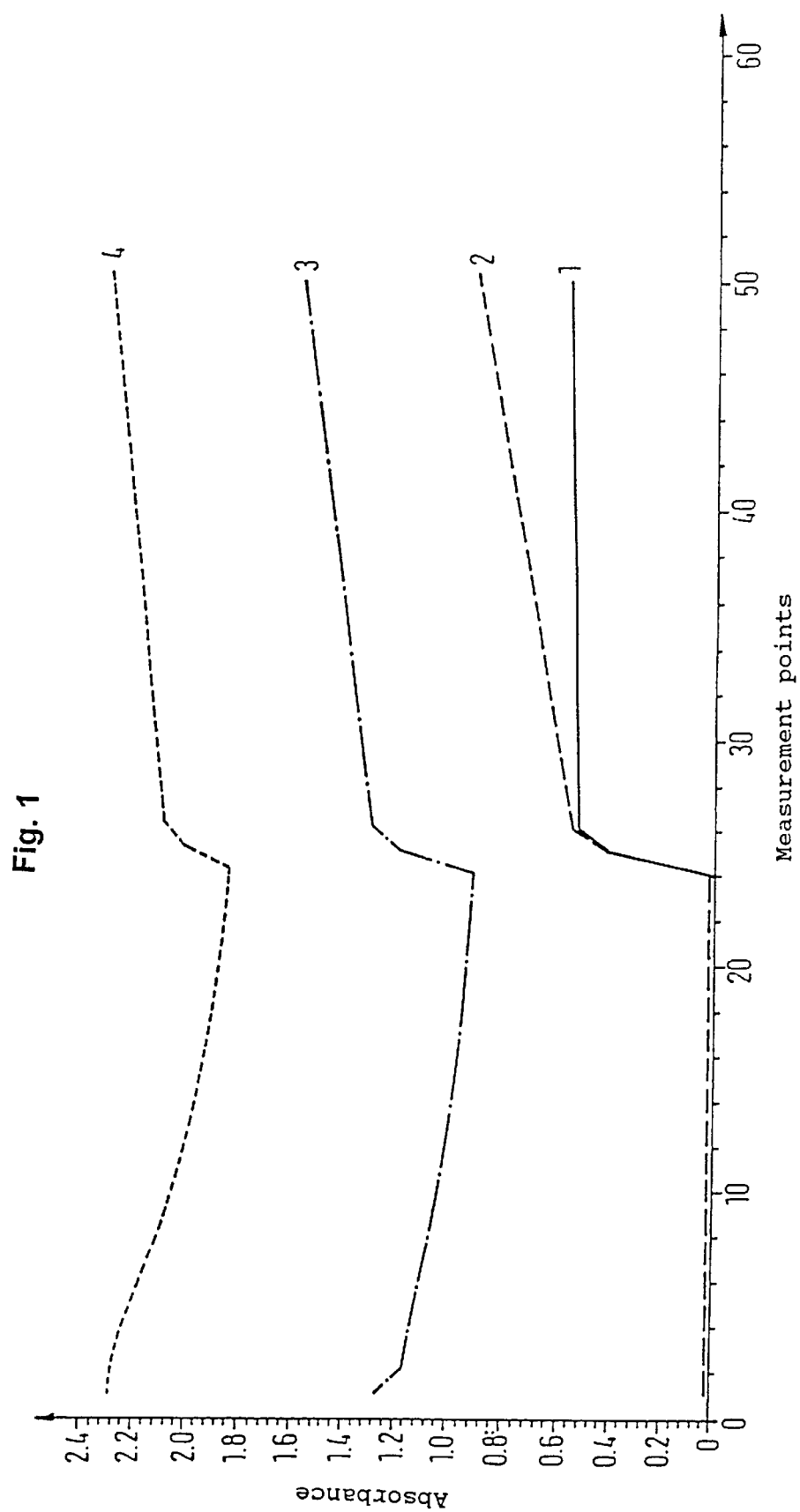
FIG. 1 shows the time course of the measured signal in a determination of alkaline phosphatase in samples containing different amounts of haemoglobin derivative without the addition of a peroxidic compound.

1.4.1. Reaction kinetics (absorbance time course):

FIG. 1 shows the absorbance time course in the alkaline phosphatase test when using the basic reagent (1.2.1) and the following samples:

curve 1: 0.9% NaCl (=reagent blank)

curve 2: serum without DClHb curve 3: serum containing 1000 mg/dl DClHb curve 4: serum containing 2000 mg/dl DClHb At least with the serum with a DClHb content of 2000 mg/dl an initial absorbance of 2.3 is reached which is at the photometric detection limit and no longer allows a reliable determination of the enzyme activity.

Figure 2:
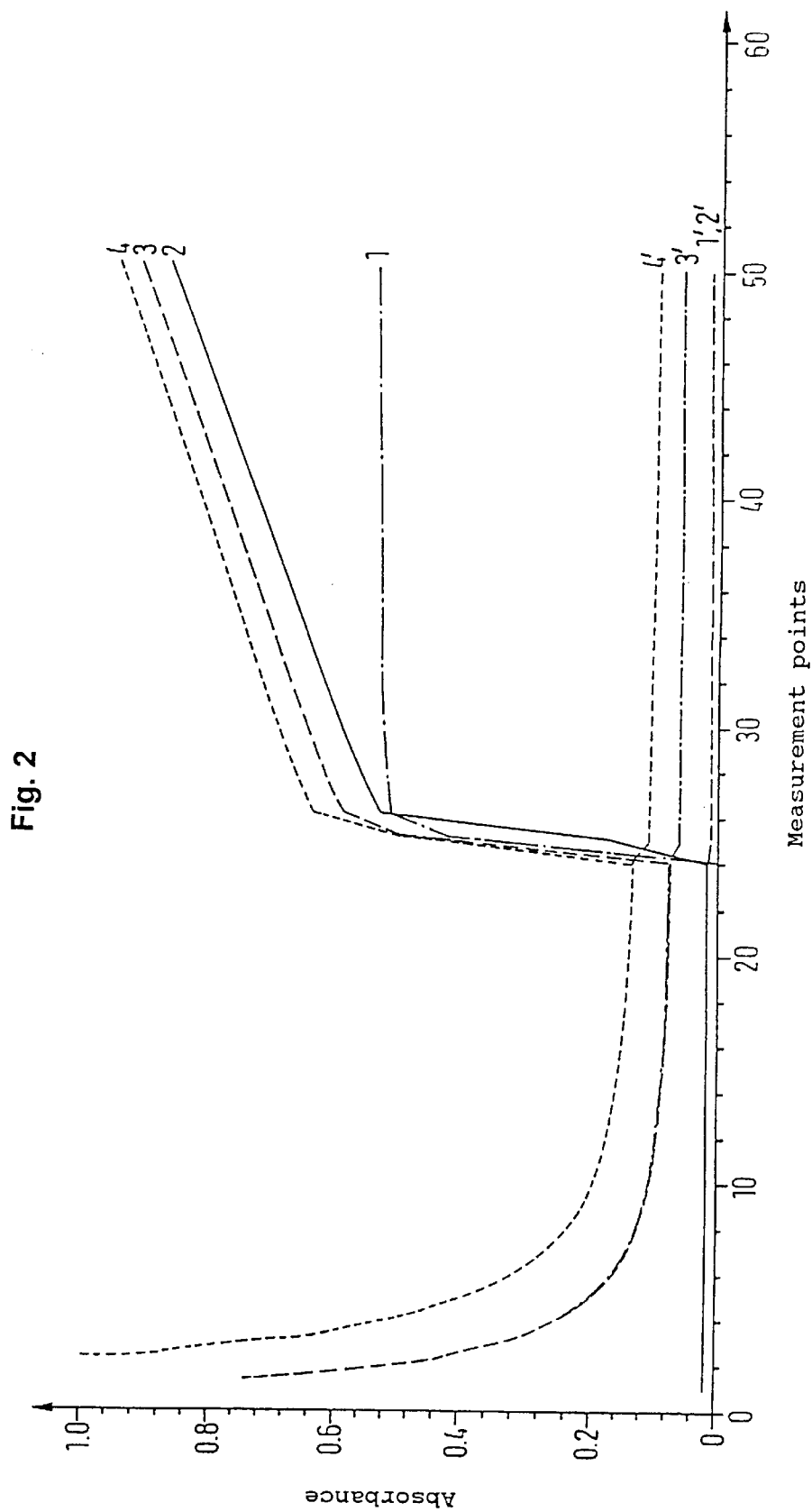
FIG. 2 shows the time course of the measured signal in a determination of alkaline phosphatase in samples containing different amounts of haemoglobin derivative with the addition of a peroxidic compound (1-4) or the time course of the measured signal for a blank correction (1'-4')

In contrast, as shown in FIG. 2 (assignment of the absorbance time courses to the various samples as in FIG. 1) the presence of peroxide in R1 of the alkaline phosphatase reagent leads to a rapid decrease of the initial absorbance caused by the haemoglobin derivative so that an initial absorbance of less than 0.2 is reached at the start of the measurement interval (measuring point 30) even with the serum spiked with DClHb to a concentration of 2000 mg/dl. A further haemoglobin bleaching which may still underly the colour formation from the chromogenic substrate during the measurement interval can be determined by additionally measuring a separate reaction mixture with chromogen-free R2 (=R1 from the basic reagent) and using this to correct the AP activity (curves 1'–4' of FIG. 2).

1.4.2. Alkaline phosphatase recovery

The following table lists the data for the recovery of alkaline phosphatase in the serum pool spiked with various DClHb amounts when using (a) the conventional AP reagent and (b) the AP reagent to which $H_2O_2$ was added to R1:

| | | | | Recovery of alkaline phosphatase* | | | |
|---|---|---|---|---|---|---|---|
| | | | | | Reagent with $H_2O_2$ addition | | |
| | DClHb con- | Reagent without | | without blank value | | with blank value | |
| Sample | centration | $H_2O_2$ addition | | correction | | correction | |
| No. | (mg/dl) | U/l | % | U/l | % | U/l | % |
| 1 | 0 | 275 | (100) | 272 | 99 | 272 | 99 |
| 2 | 200 | 254 | 92 | 272 | 99 | 273 | 99 |
| 3 | 400 | 239 | 87 | 268 | 98 | 270 | 98 |
| 4 | 600 | 232 | 84 | 265 | 96 | 269 | 98 |
| 5 | 800 | 216 | 78 | 262 | 95 | 267 | 97 |
| 6 | 1,000 | 200 | 73 | 262 | 95 | 268 | 98 |
| 7 | 1,200 | 188 | 68 | 259 | 94 | 267 | 97 |
| 8 | 1,400 | 176 | 64 | 262 | 95 | 272 | 99 |
| 9 | 1,600 | 162 | 59 | 258 | 94 | 268 | 98 |
| 10 | 1,800 | 146 | 53 | 257 | 94 | 271 | 99 |
| 11 | 2,000 | 139 | 50 | 249 | 91 | 262 | 95 |

*In each case the tests were calibrated with a calibrator for automated systems, Boehringer Mannheim GmbH, Order No. 759 350.

The table shows that the recovery of alkaline phosphatase using the conventional analytical reagent decreases considerably with increasing sample concentrations of haemoglobin derivative, whereas with the peroxide addition according to the invention it is still over 90% (calculated without a blank value correction) or ≧95% (calculated with blank value correction) even at 2000 mg/dl DClHb/dl.

Identical results are also obtained if the serum pool is spiked with the haemoglobin derivative from the Somatogen Co. (recombinant human haemoglobin derivative from *E. coli* with an intramolecular di-α fusion) instead of with DClHb.

The result also does not change if sodium perborate ($NaBO_2.H_2O_2.3\ H_2O$) is added instead of $H_2O_2$ as the peroxide; e.g. at perborate concentrations of 14.4 or 28.8 mmol/l R1 (final concentration in the test=11.8 or 23.6 mmol/l) the following AP recoveries were measured:

| | | Recovery of alkaline phosphatase (%) | | |
|---|---|---|---|---|
| Sample | DClHb content (mg/dl) | R1 without perborate | R1 with perborate 14.4 mmol/l | R1 with perborate, 28.8 mmol/l |
| 1 | 0 | (100) | 103* | 103* |
| 2 | 2000 | 67 | 101* | 102* |

*) corrected by subtracting the kinetic blank value (test mixture with chromogen-free R2)

Finally similar results were obtained when for example catalase was additionally added to R2 to degrade the peroxide.

EXAMPLE 2

Determination of α-amylase in serum containing a haemoglobin derivative.

2.1. Sample material

Type and preparation of example 1, item 1.1.

2.2. Reagents

2.2.1. Amylase basic reagent:

α-amylase EPS liquid (Sys 2 pack, Boehringer Mannheim GmbH, order No. 1555 693), composition:

| R1: | α-glucosidase | > 4 U/ml |
| | HEPES BUFFER (pH 7.15) | 52.5 mmol/l |
| | NaCl | 87.0 mmol/l |
| | MgCl$_2$ | 12.6 mmol/l |
| R2: | 4,6-ethylidene-G7 PNP | 22.0 mmol/l |
| | HEPES buffer (pH 7.15) | 52.5 mmol/l |

2.2.2. Amylase reagent with peroxide additive:

Like 2.2.1. except that H$_2$O$_2$ is additionally added to R1 at a concentration of 147 mmol/l (0.5 ml 30% perhydrol per 30 ml R1) (H$_2$O$_2$ final concentration in the test=118 mmol/l).

2.3. Procedure for the determination

Amylase was determined on a Boehringer Mannheim/Hitachi 717 analyser at 37° C. with the instrument settings according to the working instructions of the package insert (10 μl sample, 250 μl R$_1$, 50 μl R2; wavelengths 700/405 nm; measurement interval 40th–50th measurement point).

Figure 3:
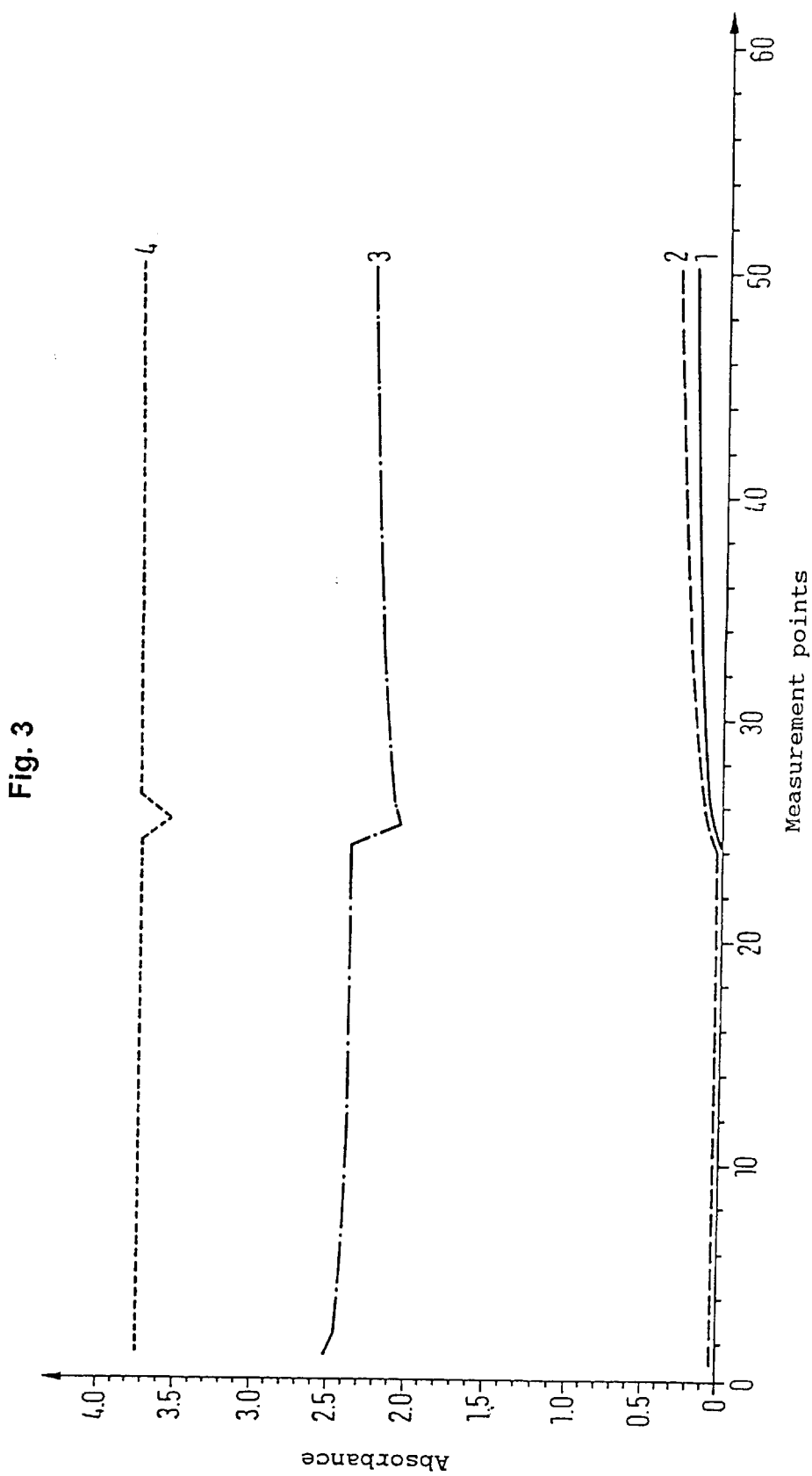
FIG. 3 shows the time course of the measured signal in a determination of α-amylase in samples containing different amounts of haemoglobin derivative without the addition of a peroxidic compound.

2.4. Results 2.4.1. Reaction kinetics (absorbance time course):

FIG. 3 shows the absorbance time course in the amylase test when using the basic reagent (2.2.1) and the following samples:

curve 1: 0.9% NaCl (=reagent blank value)

curve 2: serum without DClHb curve 3: serum containing 1000 mg/dl DClHb curve 4: serum containing 2000 mg/dl DClHb FIG. 3 shows that a base absorbance of more than 2 is reached in the conventional amylase test even at a DClHb concentration of 1000 mg/dl whereas the measuring range of the photometer is exceeded with the sample spiked with DClHb to 2000 mg/dl and thus a determination of amylase is completely impossible.

Figure 4:
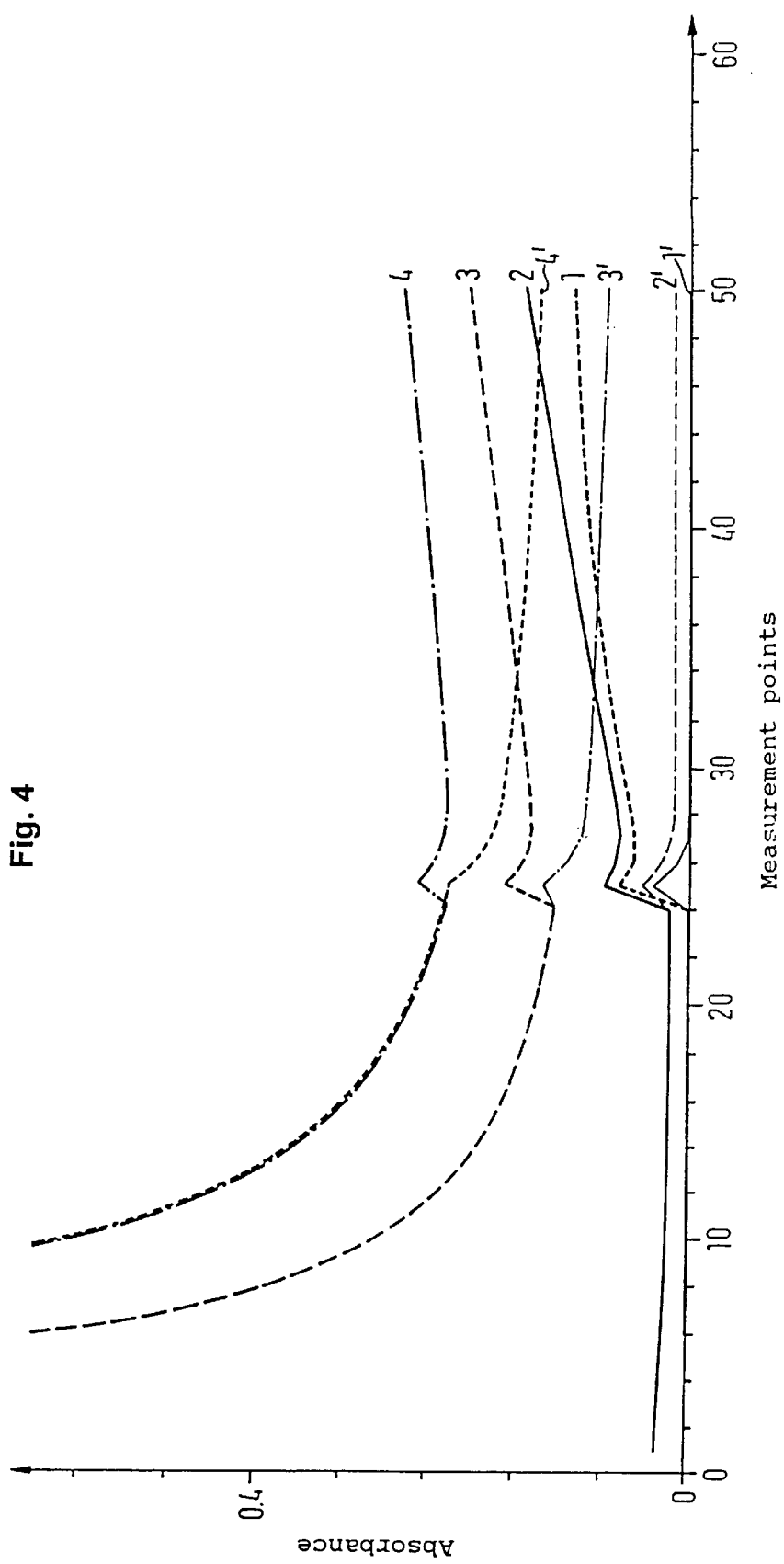
FIG. 4 shows the time course of the measured signal in a determination of a-amylase in samples containing different amounts of haemoglobin derivative with the addition of a peroxidic compound (1-4) or the time course of the measured signal for a blank correction (1'-4')

In contrast, as shown in FIG. 4 (assignment of the various absorbance time courses to the sample material as in FIG. 3) the addition of peroxide to R1 of the amylase reagent leads to a rapid decrease of the initial absorbance caused by the haemoglobin derivative so that an initial absorbance of less than ca. 0.3 is reached at the start of the measurement interval (measuring point 40) even with the serum spiked with DClHb to 2000 mg/dl. Like the AP determination it is also advisable in this case to also measure a separate reaction mixture with chromogen-free R2 (=R1 from the basic reagent) and using this as a correction when calculating the amylase activity (curves 1'–4' of FIG. 4) in order to take a further haemoglobin bleaching in the measurement window into account.

2.4.2. Amylase recovery

The following table lists the data for the recovery of amylase in the serum pool spiked with various DClHb amounts when using (a) the conventional amylase reagent and (b) the amylase reagent to which H$_2$O$_2$ was added to R1:

| | | Recovery of amylase* | | | |
| --- | --- | --- | --- | --- | --- |
| Sample | DClHb concentration | Reagent without H$_2$O$_2$ addition | | Reagent with H$_2$O$_2$ addition** | |
| No. | (mg/dl) | U/l | % | U/l | % |
| 1 | 0 | 122 | (100) | 119 | 98 |
| 2 | 200 | 95 | 78 | 114 | 93 |
| 3 | 400 | 79 | 65 | 120 | 98 |
| 4 | 600 | 84 | 69 | 117 | 96 |
| 5 | 800 | 76 | 62 | 115 | 94 |
| 6 | 1000 | 83 | 68 | 113 | 93 |
| 7 | 1200 | 88 | 72 | 117 | 95 |
| 8 | 1400 | 86 | 71 | 114 | 93 |
| 9 | 1600 | 69 | 57 | 112 | 92 |
| 10 | 1800 | 65 | 53 | 111 | 91 |
| 11 | 2000 | −13 | −11 | 112 | 92 |

*) In each case the tests were calibrated with a calibrator for automated systems, Boehringer Mannheim GmbH, Order No. 759 350

**) corrected by subtracting the kinetic blank value (test mixture with chromogen-free R2).

The table shows that the recovery of amylase with the conventional reagent decreases considerably with increasing DClHb concentrations and negative values are even obtained at 2000 mg/dl, whereas with the peroxide addition according to the invention it is still over 90%.

Otherwise the comments made for the AP determination also apply.

EXAMPLE 3

Determination of γ-glutamyl transferase (γ-GT) in serum containing haemoglobin derivative 3.1. Sample Material Type and preparation of example 1, item 1.1.

3.2. Reagents 3.2.1. γ-GT basic reagent:

Gamma-GT (Sys 2 pack, Boehringer Mannheim GmbH, order No. 489 496), composition:

| R1: | NaOH | 76 mmol/l |
| --- | --- | --- |
| | glycylglycine (pH 7.7) | 150 mmol/l |
| R2: | L-γ-glutamyl-3-carboxy-4-nitroanilide | 6 mmol/l R1 |

3.2.2. γ-GT reagent with peroxide additive:

Like 3.2.1. except that H$_2$O$_2$ is additionally added to R1 at a concentration of 147 mmol/l (0.5 ml 30% perhydrol per 30 ml R1) (H$_2$O$_2$ final concentration in the test=116 mmol/l).

3.3. Procedure for the γ-GT determination:

The γ-GT was determined on a Boehringer Mannheim/Hitachi 717 analyser at 37° C. with the instrument settings according to the working instructions of the package insert (15 μl sample, 250 μl R1, 50 μl R2; wavelengths 660/405 nm; measurement interval 30th–50th measurement point).

Figure 5:
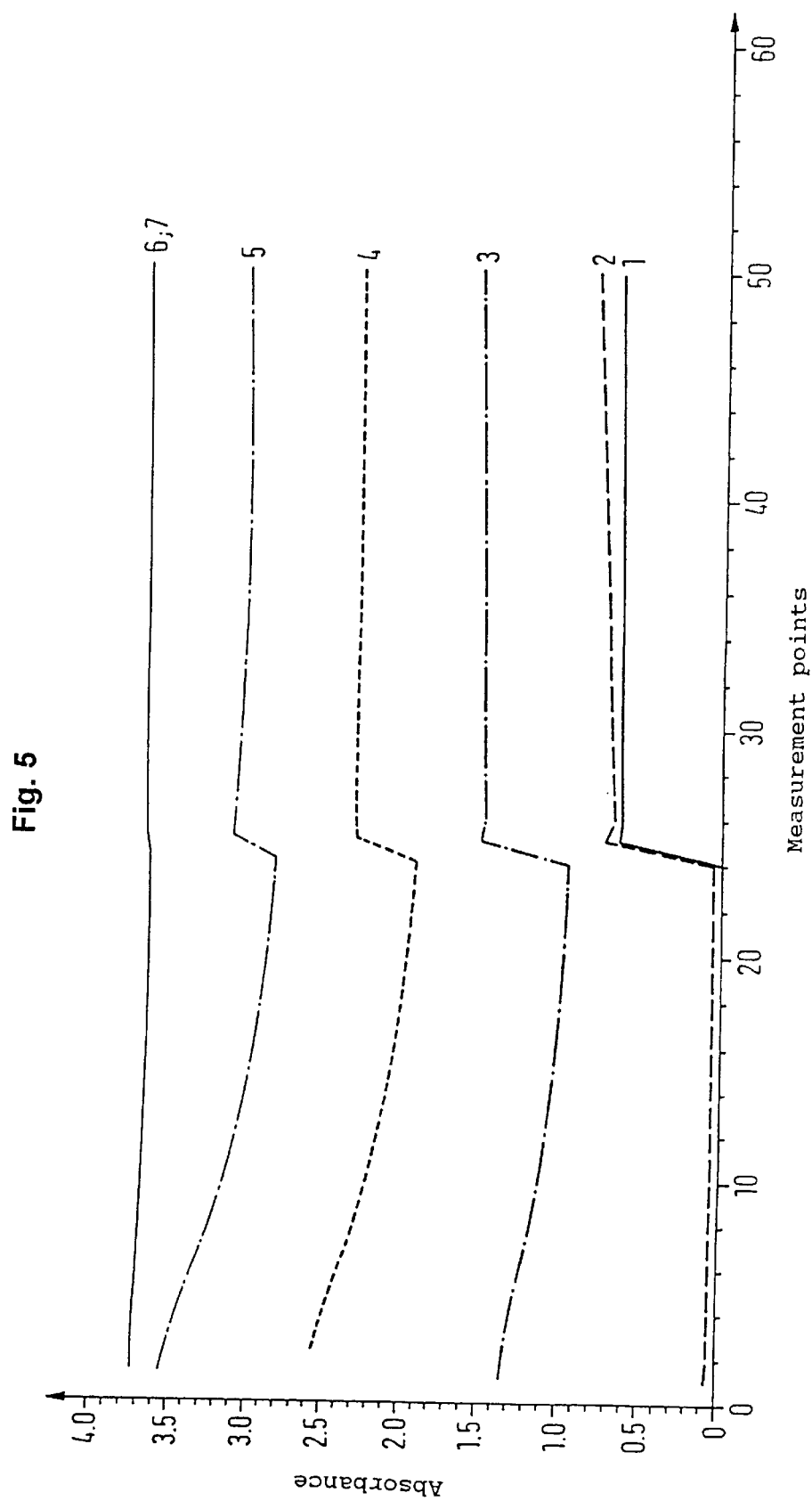
FIG. 5 shows the time course of the measured signal in a determination of γ-GT in samples containing different amounts of haemoglobin derivative without the addition of a peroxidic compound.

3.4. Results 3.4.1. Reaction kinetics (absorbance time course):

FIG. 5 shows the absorbance time course in the γ-GT test when using the basic reagent (3.2.1) and the following samples:

curve 1: 0.9% NaCl (=reagent blank value)

curve 2: serum without DClHb curve 3: serum containing 400 mg DClHb/dl curve 4: serum containing 800 mg DClHb/dl curve 5: serum containing 1200 mg DClHb/dl curve 6: serum containing 1600 mg DClHb/dl curve 7: serum containing 2000 mg DClHb/dl FIG. 5 shows that a base absorbance of more than 2 is already reached in the conventional γ-GT test at a DClHb concentration of 800 mg/dl whereas the measuring range of the photometer is exceeded by the samples spiked with more than 1600 mg/dl DClHb and thus from the outset it is no longer possible to determine γ-GT.

Figure 6:
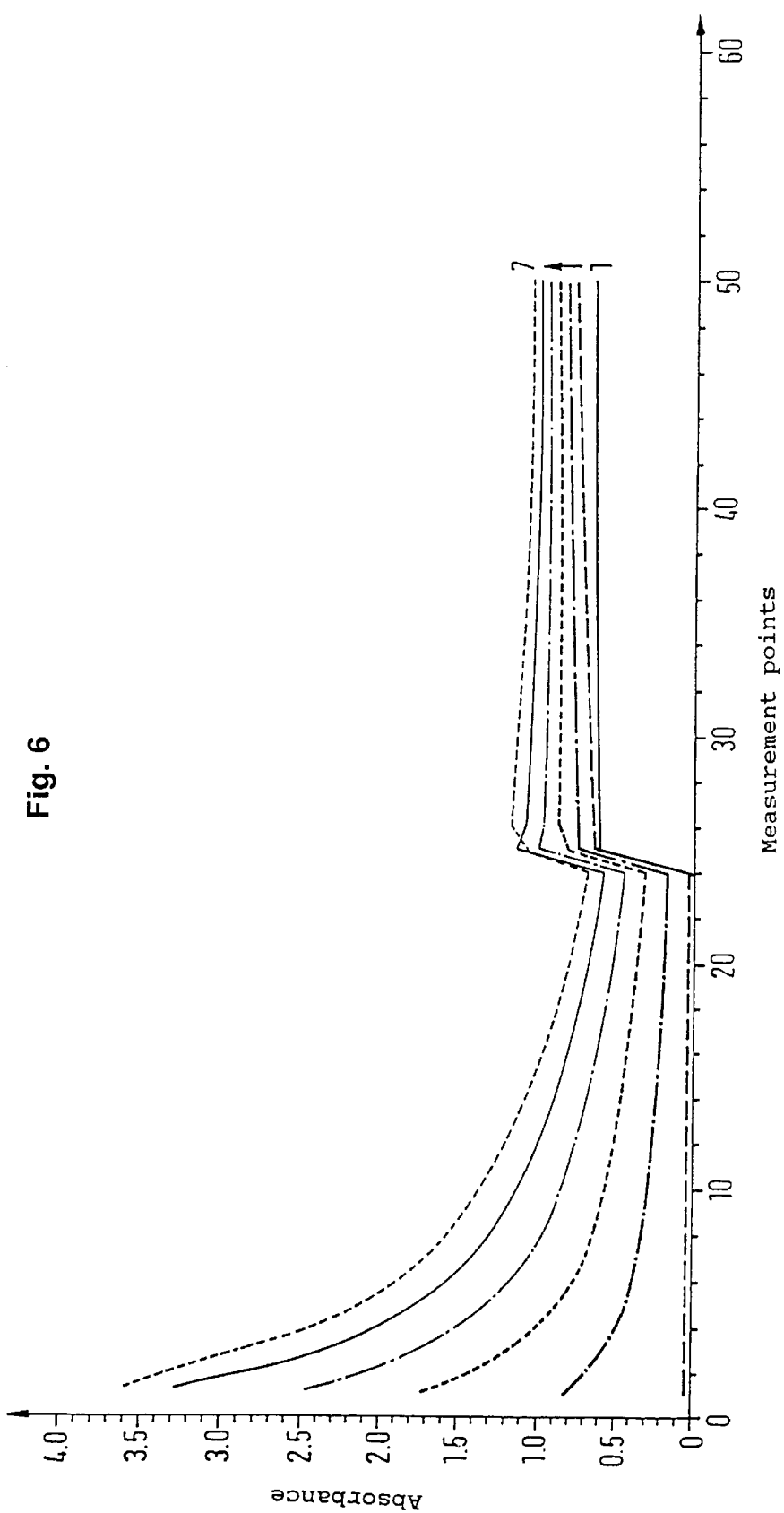

In contrast, as shown in FIG. 6 (assignment of the absorbance time courses to the various samples as in FIG. 5) the presence of peroxide in R1 of the γ-GT reagent leads to a rapid decrease of the initial absorbance caused by the haemoglobin derivative so that an initial absorbance of less than 1 is reached at the start of the measurement interval (measuring point 30) even with the serum spiked with DClHb to 2000 mg/dl.

A further haemoglobin bleaching effect which may still underly the colour signal from the conversion of the chromogenic substrate can also in this case be determined analogously to examples 1 and 2 in a parallel test mixture with 1 containing $H_2O_2$ and with R1 of the base reagent as chromogen-free R2 (curves 1'-7' of FIG. 7) and taken into account when calculating the γ-GT recovery.

3.4.2. γ-GT recovery

The following table lists the data for the γ-GT recovery in the serum pool spiked with various DClHb amounts when using (a) the conventional γ-GT reagent and (b) the γ-GT reagent to which $H_2O_2$ was added to R1:

| Sample No. | DClHb concentration (mg/dl) | Reagent without $H_2O_2$ addition U/l | Reagent without $H_2O_2$ addition % | Reagent with $H_2O_2$ addition** U/l | Reagent with $H_2O_2$ addition** % |
|---|---|---|---|---|---|
| 1 | 0 | 53.3 | (100) | 52.3 | 98 |
| 2 | 200 | 31.9 | 60 | 49.6 | 93 |
| 3 | 400 | 17.0 | 32 | 48.2 | 90 |
| 4 | 600 | −1.7 | −3 | 49.8 | 93 |
| 5 | 800 | −9.1 | −17 | 48.5 | 91 |
| 6 | 1000 | −24.8 | −47 | 48.1 | 90 |
| 7 | 1200 | −30.0 | −56 | 49.4 | 93 |
| 8 | 1400 | −30.1 | −56 | 51.9 | 97 |
| 9 | 1600 | −9.5 | −18 | 51.8 | 97 |
| 10 | 1800 | −10.4 | −19 | 50.0 | 94 |
| 11 | 2000 | −10.3 | −19 | 50.8 | 95 |

*) In each case the tests were calibrated with a calibrator for automated systems, Boehringer Mannheim GmbH, Order No. 759 350
**) corrected by subtracting the kinetic blank value test mixture with chromogen-free R2)

The able shows that the recovery of γ-GT with the conventional reagent decreases very rapidly with increasing DClHb concentrations and already results in negative values above 600 mg/dl, whereas with the reagent containing the peroxide addition according to the invention it is always>90%.

Furthermore with regard to the results obtained with the heamoglobin derivative from the Somatogen Co., the use of sodium perborate instead of $H_2O_2$ and the optional addition of catalase to R2, the statements made for the AP determination apply analogously.

We claim:

1. A method for the elimination or/and reduction of interferences which are caused by the presence of free haemoglobin in the determination of an analyte in a sample by optical measurement, wherein one or several peroxidic compounds are added to the reagent used to determine the analyte or to a part thereof.

2. The method as claimed in claim 1, wherein
inorganic peroxidic compounds are used.

3. The method as claimed in claim 2, wherein
the peroxidic compounds are selected from the group consisting $H_2O_2$ and perborates.

4. The method as claimed in claim 1, wherein
the optical measurement is carried out at at least one measurement wavelength at which haemoglobin has an absorption.

5. The method as claimed in claim 4, wherein
the optical measurement is carried out at measurement wavelengths of 380–450 nm or/and 520–590 nm.

6. The method as claimed in claim 1, wherein
an analyte is determined selected from the group consisting of α-amylase, alkaline phosphatase and γ-glutamyl transferase.

7. The method as claimed in claim 1, wherein
the final concentration of peroxidic compounds in the test mixture is 1–500 mmol/l with respect to the content of $O_2^{2-}$.

8. The method as claimed in claim 7, wherein
the final concentration is 5–200 mmol/l.

9. The method as claimed in claim 1, wherein
the duration of action of the peroxidic compounds on the sample before measurement is at least 1 minute.

10. The method as claimed in claim 1, wherein
the analyte determination is carried out as a multi-step test in which at least two partial reagents are added at different times to the sample.

11. The method as claimed in claim 10, wherein
the peroxidic compounds are added together with the first partial reagent.

12. The method as claimed in claim 1, wherein
a sample is determined which contains a blood substitute.

13. The method as claimed in claim 1, wherein
the determination is carried out on a serum or plasma sample.

14. The method as claimed in claim 1, wherein
the determination is carried out in an automated analyzer.

15. The method as claimed in claim 1, wherein
the measurement signal obtained in the analyte determination is subjected to a blank value correction.

16. The method as claimed in claim 15, wherein
the kinetic blank value is subtracted from the measurement signal.

17. A reagent kit for the determination of an analyte in a sample by optical measurement, wherein
in addition to the components required for the analyte determination, it contains at least one peroxidic compound to eliminate or/and reduce interferences which are caused by free haemoglobin.

18. The reagent kit as claimed in claim 17, wherein
it is composed of at least two partial reagents that are spatially separated from one another in which one partial reagent contains the peroxidic compound and the other partial reagent or reagents contain additional test components.

19. The reagent kit as claimed in claim 17 for the determination of α-amylase preferably comprising a first partial reagent which contains the peroxidic compound, a second partial reagent which contains a suitable buffer and optionally an α-amylase auxiliary enzyme or/and an antibody and a further partial reagent which contains a chromogenic α-amylase substrate.

20. The reagent kit as claimed in claim 17 for the determination of alkaline phosphatase comprising a first partial reagent containing a peroxidic compound, a second partial reagent which contains a suitable buffer and a further partial reagent which contains a chromogenic substrate for alkaline phosphatase.

21. The reagent kit as claimed in claim 17 for the determination of γ-glutamyl transferase comprising a first partial reagent containing a peroxidic compound, a second partial reagent which contains a suitable buffer and a further partial reagent which contains a chromogenic substrate for γ-glutamyl-transferase.

* * * * *